(12) United States Patent
Kiss

(10) Patent No.: US 7,423,029 B1
(45) Date of Patent: Sep. 9, 2008

(54) COMPOUNDS TO PROMOTE REGENERATION OF BONE MARROW

(75) Inventor: Zoltan Kiss, Austin, MN (US)

(73) Assignee: Zoltan Laboratories, LLC, Austin, MN (US)

( * ) Notice: Subject to any disclaimer, the term of this patent is extended or adjusted under 35 U.S.C. 154(b) by 0 days.

(21) Appl. No.: 11/690,260

(22) Filed: Mar. 23, 2007

(51) Int. Cl.
*A61K 31/33* (2006.01)
*A61K 31/38* (2006.01)

(52) U.S. Cl. .................................... 514/183; 514/437
(58) Field of Classification Search ................ None
See application file for complete search history.

(56) References Cited

U.S. PATENT DOCUMENTS

2005/0004038 A1 1/2005 Lyon et al.

FOREIGN PATENT DOCUMENTS

| EP | 0342433 | 11/1989 |
|---|---|---|
| WO | 2007076592 | 10/2001 |

OTHER PUBLICATIONS

Ballestrero et al., "Comparative Effects of Three Cytokine Regimens After High-Dose Cyclophosphamide: Granulocyte Colony-Stimulating Factor, Granulocyte-Macrophage Colony-Stimulating Factor (GM-CSF), and Sequential Interleukin-3 and GM-CSF," J. Clin. Oncol., vol. 17, pp. 1296-1303, Apr. 1999.

Fox et al., "Thrombopoietin expands hematopoietic stem cells after transplantation," J. Clin. Invest., vol. 110, No. 3, pp. 389-394, Aug. 2002.
Dai et al., "A Potential Synergistic Anticancer Effect of Paclitaxel and Amifostine on Endometrial Cancer," Cancer Res., vol. 65, No. 20, pp. 9517-9524, Oct. 2005.
Chen et al., "Pharmacokinetics and Biologic Activity of the Novel Mast Cell Inhibitor, 4-(3'-Hydroxyphenyl)-amino-6,7-dimethoxyquinazoline in Mice," Pharmaceutical Res., vol. 16, No. 1, pp. 117-122, 1999.
Bickford et al., "Nutraceuticals Synergistically Promote Proliferation of Human Stem Cells," Stem Cells and Development, vol. 15, pp. 118-123, 2006.
Vas et al., "Biphasic Effect of Recombinant Galectin-1 on the Growth and Death of Early Hematopoietic Cells," Stem Cells, vol. 23, pp. 279-287, 2005.
Pittenger et al., "Multilineage Potential of Adult Human Mesenchymal Stem Cells," Stem Cells, Science, vol. 284, pp. 143-147, Apr. 1999.
Carmichael et al., "Evaluation of Tetrazolium-based Semiautomated Colormetric Assay: Assesment of Chemosensitivity Testing," Cancer Res., vol. 47, pp. 936-942, Feb. 1987.
Winter et al., "Evaluation and lead optimization of anti-malarial acridones," Experimental Parasitology 114(1): 47-56, 2006.
International Search Report and Written Opinion of international application No. PCT/US2007/064761, mailed Nov. 28, 2007, 9 pp.

*Primary Examiner*—Raymond J Henley, III
(74) *Attorney, Agent, or Firm*—Faegre & Benson LLP

(57) ABSTRACT

Embodiments of the present invention include the use of heterocyclic trialkyl ammonium-containing compounds to promote regeneration of bone marrow from endogenous or exogenous stem/progenitor cells and to normalize blood cell and platelet counts.

20 Claims, No Drawings

COMPOUNDS TO PROMOTE REGENERATION OF BONE MARROW

FIELD OF THE INVENTION

The invention provides heterocyclic trialkyl ammonium-containing compounds, such as [3-(3,4-dimethyl-9-oxo-9H-thioxanthen-2-yloxy)-2-hydroxypropyl]trimethylammonium chloride, or CCompound1, N,N,-diethyl-N-methyl-2-[9-oxo-9H-thioxanthen-2-yl)methoxy]ethanaminium iodide, or CCompound3, and N,N-Diethyl-N-allyl-3-(2-methyl-9H-thioxanthen-9-ylidene)-propane-1-aminium bromide, or CCompound26 to promote bone marrow regeneration from endogenous stem/progenitor cells after administering chemotherapy or radiation treatment, or from external stem/progenitor cells after administering lethal total body irradiation and/or high dose chemotherapy followed by transplantation of bone marrow stem/progenitor cells.

BACKGROUND

Differentiated blood cells are formed from hematopoietic (blood-forming) pluripotent stem cells via intermediate stem cell-derived progenitor cells. Differentiated blood cells can be classified as red blood cells (RBC) or erythrocytes and white blood cells (WBC) or leukocytes. The blood also contains platelets that are detached cell fragments of much larger cells called megakaryocytes. The erythrocytes' main function is to transport oxygen and carbon dioxide bound to hemoglobin. White blood cells are grouped into three major categories including granulocytes, monocytes, and lymphocytes. Based on their morphology, granulocytes are also subdivided into three classes i.e. neutrophils, basophils and eosinophils. The monocytes mature into macrophages that together with neutrophils are the major phagocytes playing important roles in fighting infection. There are two classes of lymphocytes, i.e. T lymphocytes and B lymphocytes, both significantly contributing to immune responses.

Clonogenic committed hematopoietic progenitors give rise to the formation of homogenous populations of blood cells. For example, granulocyte-colony forming unit (CFU-G) cells give rise to a homogenous population of neutrophils, basophils and eosinophils. M-colony forming unit (CFU-M) cells give rise to a homogeneous population of macrophages, while granulocyte, macrophage-colony forming unit (CFU-GM; also often indicated as GM-CFU) cells give rise to macrophages and various subclasses of granulocytes.

There are many diseases and treatment regimens that can lead to anemia and some form of cytopenia often leading to further deterioration of physiological condition. These include hematopoietic cancers, solid cancers that metastasized to the bone marrow, AIDS, and treatments with radiation or chemotherapy. Most established anticancer and many anti-HIV drugs produce severe myelotoxicity that limits their clinical usefulness. In fact many prospective drug candidates cannot be introduced into the clinical practice because of their bone marrow toxicity that in most cases results in neuotropenia or thrombocytopenia.

There are relatively few safe tools to help recovery of bone marrow function during or after intensive radiation or chemotherapy. Erythropoietin (EPO) at doses of 150-300 Unit per kg administered three times a week is effective in reducing anemia and the requirement for blood cell transfusion. However, EPO does not significantly affect formation of platelets or blood cells of myeloid origin. In contrast, granulocyte-colony stimulating factor (G-CSF) or granulocyte-macrophage colony-stimulating factor (GM-CSF) can reduce the duration and severity of cyclophosphamide-induced neutropenia. Ballestrero, A., Ferrando, F., Garuti, A., Basta, P., Gonella, R., Stura, P., Mela, G. S., Sessarego, M, Gobbi, M. and Patrone, F., "Comparative effects of three cytokine regimens after high-dose cyclophosphamide: Granulocyte colony-stimulating factor, granulocyte-macrophage colony-stimulating factor (GM-CSF), and sequential interleukin-3 and GM-CSF," *J. Clin. Oncol.*, 17, 1296-1303 (1999).

Thrombopoietin (TPO), initially described as a regulator of megakaryocyte and platelet formation, is a growth factor that accelerates the recovery of all hematopoietic lineages following myelosuppressive therapies and that can expand hematopietic stem cells after transplantation. Fox, N., Priestley, G., Papayannopoulou, T. and Kaushansky, K., "Thrombopoietin expans hematopoietic stem cells after transplantation," *J. Clin. Invest.*, 110, 389-394 (2002). However, such role so far could be proved only for endogenous TPO; unfortunately, TPO administration not only failed to promote hematological recovery after chemotherapy or bone marrow transplantation, but it was also shown to cause immunological complications.

Amifostine is another drug that protects normal blood profile in paclitaxel-treated endometrial cancer. Dai, D., Holmes, A. M., Nguyen, T., Davies, S., Theele, D. P., Verschraegen, C. and Leslie, K. K., "A potential synergistic anticancer effect of paclitaxel and amifostine on endometrial cancer," *Cancer Res.*, 65, 9517-9524 (2005). This agent, however, only prevents drug-induced death of differentiated blood cells and does not promote hematopoiesis.

SUMMARY OF THE INVENTION

One embodiment of the invention includes a method of regenerating bone marrow by administering a composition to a subject that includes a heterocyclic compound, thereby normalizing blood cell and platelet counts, wherein the compound is a chemically synthesized heterocyclic compound (hereinafter referred to as "CC compounds") that contains a quaternary ammonium group.

DETAILED DESCRIPTION OF THE INVENTION

The agents used in embodiments of the invention are chemically synthesized heterocyclic compounds (hereinafter referred to as "CC compounds") that contain a quaternary ammonium group. The specific compounds used in the invention are thioxanthones and thioxanthenes. Previously recognized effects of representative CC compounds, such as the thioxanthones CCompound1 and CCompound3, include their ability to decrease or prevent tumor- and chemotherapy-induced reduction in body weight.

In one embodiment, the present invention provides a CC compound to promote regeneration of bone marrow and hematological recovery after sublethal radiation treatment or chemotherapy. For this use, the CC compound is preferably administered both before and after the respective treatment.

In another embodiment, a CC compound is provided to promote regeneration of bone marrow and hematological recovery after lethal total body irradiation and/or high intensity chemotherapy followed by bone marrow transplantation. In this embodiment, the CC compound is preferably administered shortly before, during, or shortly after bone marrow transplantation.

Both CCompound1 and CCompound3 are soluble in water and are suitable for oral application in the form of tablets, gel capsules and the like. They also can be administered by one of the available injection methods or by using a subcutaneously inserted minipump.

Sublethal irradiation and many chemotherapeutic regimens, such as cyclophosphamide, cause significant damage to the bone marrow resulting in myelosuppression, i.e. decreased formation of granulocytes and macrophages. Such treatments also decrease the formation of red blood cells and megakaryocytes/platelets. Significantly altered blood profile then leads to other complications such as extreme loss of body weight.

Embodiments of the invention show that treatment of mice with cyclophosphamide leads to reductions in the white blood cell and platelet counts and that CCompound1, CCompound3 and CCompound26 each can decrease the effects of cyclophosphamide. Similarly, all these compounds are shown to prevent, although with different efficacy, body weight loss induced by mammary cancer and cyclophosphamide. Accordingly, these compounds are suitable to improve the blood profile of chemotherapy-treated subjects.

Embodiments of the invention provide evidence that pretreatment of mice with a CC compound subjected to sublethal irradiation promotes the recovery of granulocyte-macrophage colony-stimulating cells, an indication of increased level of re-population of bone marrow. The results imply that treatment with an appropriate CC compound, such as CCompound1, CCompound3, or CCompound26 is suitable to improve recovery of neutrophils, macrophages, and other blood cells after partial myeloablation.

Total body irradiation with a lethal dose leads to death within few days unless followed by blood marrow transplantation. Some of the transplanted stem cells home to the empty space of bone cavity and give rise to progenitors and differentiated blood cells and platelets. Embodiments of the invention show that administration of a CC compound to lethally irradiated mice that received bone marrow transplantation promotes restoration of normal blood profile most probably either via promoting homing of hematopoietic stem cells to the bone marrow and/or enhancing survival/proliferation of transplanted stem cells and progenitors. The results demonstrate that CCompound1, CCompound3, CCompound26 and presumable other related compounds listed in Table 1 are suitable to promote restoration of normal blood profile after autologous or allogeneic bone marrow stem cell transplantation.

I. The Active Compounds.

A general formula to represent the members of this class of compounds is as follows:

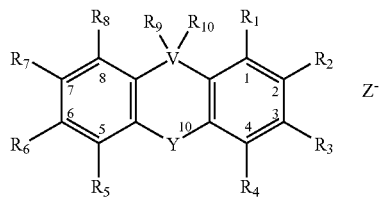

In this formula, $R_1$ and $R_{3-8}$ may be independently chosen from hydrogen or from $C_1$-$C_{26}$ straight, branched or cyclic alkanes or alkenes, aromatic hydrocarbons, alcohols, ethers, aldehydes, ketones, carboxylic acids, amines, amides, nitriles or five- and/or six-membered heterocyclic moieties or their derivatives.

Further, the variables, $R_9$ and $R_{10}$, considered or taken together may be =O or =CH—L—N$^+$($R_{11}$, $R_{12}$, $R_{13}$), where —L—N$^+$($R_{11}$, $R_{12}$, $R_{13}$) is defined below. In addition, $R_9$ and $R_{10}$ independently may be —OH or —L—N$^+$($R_{11}$, $R_{12}$, $R_{13}$).

The variables, V and Y, may be —S— or —Se—. Alternatively, the sulfur and selenium atoms in the heterocyclic moiety may further be replaced with the carbon, oxygen, or silicon atoms. In yet other embodiments, either V or Y, or both, may be nitrogen (N). In this embodiment, the —L—N$^+$($R_{11}$, $R_{12}$, $R_{13}$) group can also be attached to the N atom. For example, in phenoxazine the Y is N, and in that case the —L—N$^+$($R_{11}$, $R_{12}$, $R_{13}$) group can be linked to the N atom. Or in phenazine, when both V and Y are N, and the —L—N$^+$($R_{11}$, $R_{12}$, $R_{13}$) group can be linked to either N atoms.

In the general formula, Z$^-$ may be Cl$^-$, Br$^-$ or I$^-$.

Also, in this general formula the variable, $R_2$, may be represented by the following additional formula:

—X or —X'—L—N$^+$($R_{11}$, $R_{12}$, $R_{13}$)Z$^-$

In this additional formula, —X may be CH$_3$—CH$_2$— or —X'— may be —OCH$_2$—, —CH$_2$O—, —SCH$_2$— or —CH$_2$S—. Further, L may be $C_1$-$C_4$ straight alkane, alkene, thiol, ether, or amine.

The variables $R_{11}$, $R_{12}$ and $R_{13}$ may be represented by $C_1$-$C_4$ straight alkanes, alkenes, ethers, thiols, amines or alcohols. Preferably, the $R_{11}$, $R_{12}$, and $R_{13}$ groups are represented by methyl, ethyl, allyl, sulfhydryl, ether, amino, or hydroxyl groups or by their combinations.

The above described quaternary ammonium-containing compounds may be further altered to contain an alcohol or amine-containing X—L—N$^+$($R_{11}$, $R_{12}$, $R_{13}$) or =CH—L—N$^+$($R_{11}$, $R_{12}$, $R_{13}$) groups.

Using an appropriate heterocyclic compound, such as for example 4,7-phenanthroline or phenazine that has N atoms both in the 9th and 10th positions, L—N$^+$($R_{11}$, $R_{12}$, $R_{13}$) moieties may be attached to either N atoms.

Several subsets of thioxanthone-based and thioxanthen-based compounds were synthesized in various embodiments of the invention. Examples of the synthesized compounds include, but are not limited to (i) N,N,N-trialkyl-2-[(9-oxo-9H-thioxanthen-2-yl)methoxy]ethanaminium iodide, ii) N,N,N-trialkyl-2-[(9-oxo-9H-thioxanthen-2-yl)methoxy] propane-1-aminium iodide and iii) N,N,N-trialkyl-3-(9H-thioxanthen-9-ylidene)-propan-1-aminium iodide.

In one embodiment, the compound is [3-(3,4-Dimethyl-9-oxo-9H-thioxanthen-2-yloxy)-2-hydroxypropyl]trimethylammonium chloride, CCompound1, set out in Table 1. CCompound1 was purchased from Sigma-Aldrich.

In another embodiment, the compound is N,N-diethyl-N-methyl-2-[(9-oxo-9H-thioxanthen-2-yl)methoxy]-ethanaminium iodide, CCompound3. The CCompounds shown in Table 1 with the exception of CCompound1, have been reported in U.S. patent application No. 11,458,502, filed on Aug. 9, 2006; entitled "Compounds and Compositions to Control Abnormal Cell Growth", incorporated by reference herein.

Single treatments of healthy mice with 450 μmole (about 4.6 mg/kg) of CCompound1 or CCompound3 or daily treatments for 5 consecutive days with 400 μmole of CCompound1 or CCompound3 did not cause any significant change in the composition of various blood constituents. Similarly, such treatments did not induce significant pathological alterations in the liver, brain, kidney, heart, spleen, intestine, and lung. However, significant alterations were observed in several tissues, accompanied by the death of 20-40% of animals by day 30, at 1,000-1,500 μmole doses of CCompound1 or CCompound3. At these high doses both compounds caused mild parenchymal degeneration in the heart, focal hypostasis and chronic bronchopneumonia. Accordingly, a well tolerated maximal dose for CCompound1 or CCompound3 in mice (weighing about 25 g) is 450 μmole/animal which corresponds to a dose of 4.6 mg/kg. Therapeutically effective concentrations of CC compounds in humans will exert significant promoting effects on bone marrow regeneration without causing toxicity in other normal healthy tissues.

The thioxanthene derivative N,N-Diethyl-N-allyl-3-(2-methyl-9H-thioxanthen-9-ylidene)-propane-1-aminium bromide or CCompound26 (Table 1), (2.0 mg/kg) partially reversed cyclophosphamide-induced decrease in white blood cell and platelet counts and prevented body weight loss of cyclophosphamide-treated mammary tumor-bearing mice indicating that at this effective dose it also does not exert significant toxic effects.

Based on the similar effects of thioxanthone CCompound1 and CCompound3 as well as thioxanthene CCompound26 on blood profile and body weight, and by implication on bone marrow regeneration, all thioxanthone or thioxanthene compounds listed in Table 1 may be used to promote bone marrow regeneration.

TABLE 1

A Representative List of CCcompounds Used in Embodiments of the Invention.

| Trivial name | Chemical name | Structure |
| --- | --- | --- |
| CCcompound1 | [3-(3,4-Dimethyl-9-oxo-9H-thioxanthen-2-yloxy)-2-hydroxypropyl]trimethyl-ammonium chloride | 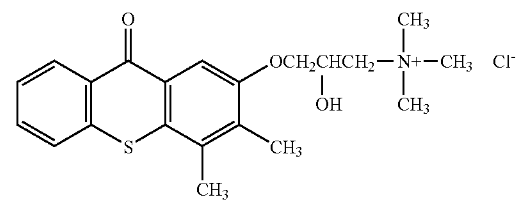 |
| CCcompound2 | N,N,N-Trimethyl-2-[(9-oxo-9H-thioxanthen-2-yl)methoxy]-ethanaminium iodide | 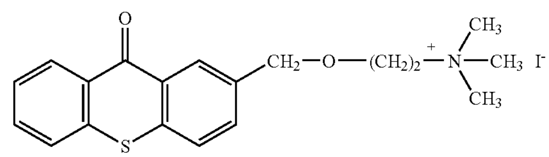 |
| CCcompound3 | N,N-Diethyl-N-methyl-2-[9-oxo-9H-thioxanthen-2-yl)methoxy]-ethanaminium iodide | 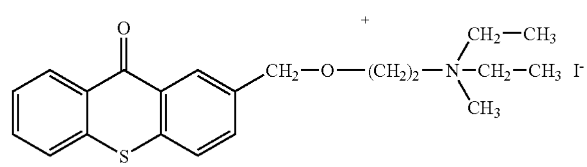 |
| CCcompound4 | N,N,N-Triethyl-2-[(9-oxo-9H-thioxanthen-2-yl)methoxy]-ethanaminium iodide | 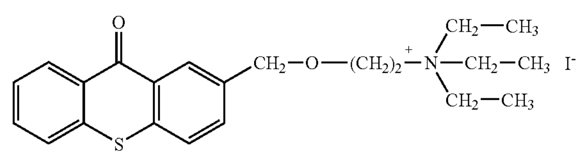 |
| CCcompound5 | N-Ethyl-N,N-dimethyl-2-[(9-oxo-9H-thioxanthen-2-yl)methoxy]-ethanaminium iodide | 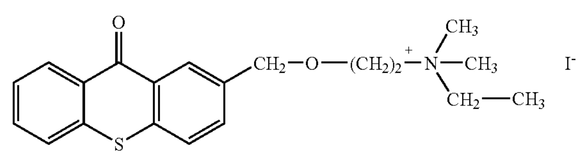 |
| CCcompound6 | 2-{[2-(Diethylamino)ethoxy]-methyl}-9H-thioxanthen-9-one hydrochloride | 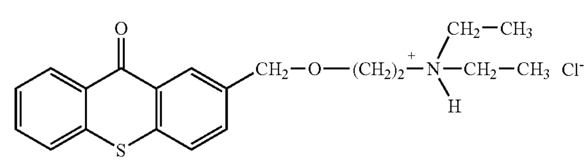 |
| CCcompound7 | N,N,N-Trimethyl-2-[(9-oxo-9H-thioxanthen-2-yl)methoxy]-propan-1-aminium iodide | 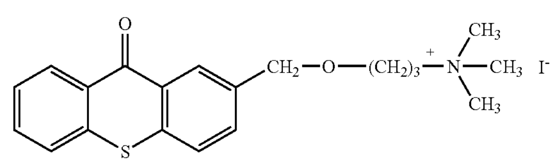 |

TABLE 1-continued

A Representative List of CCcompounds Used in Embodiments of the Invention.

| Trivial name | Chemical name | Structure |
| --- | --- | --- |
| CCcompound8 | 2-{[2-(Dimethylamino)propoxy]-methyl}-9H-thioxanthen-9-one hydrochloride | thioxanthen-9-one with $CH_2-O-(CH_2)_3-\overset{+}{N}(CH_3)_2H \quad Cl^-$ |
| CCcompound9 | N,N,N-Triethyl-3-[(9-oxo-9H-thioxanthen-2-yl)methoxy]-propane-1-aminium iodide | thioxanthen-9-one with $CH_2-O-(CH_2)_3-\overset{+}{N}(CH_2CH_3)_3 \quad I^-$ |
| CCcompound 10 | N,N-Diethyl-N-methyl-3-[(9-oxo-9H-thioxanthen-2-yl)methoxy]-propane-1-aminium iodide | thioxanthen-9-one with $CH_2-O-(CH_2)_3-\overset{+}{N}(CH_2CH_3)_2(CH_3) \quad I^-$ |
| CCcompound 11 | N,N-Dimethyl-N-ethyl-3-[(9-oxo-9H-thioxanthen-2-yl)methoxy]-propane-1-aminium iodide | thioxanthen-9-one with $CH_2-O-(CH_2)_3-\overset{+}{N}(CH_3)_2(CH_2CH_3) \quad I^-$ |
| CCcompound 12 | 2-{[3-(Diethylamino)propoxy]-methyl}-9H-thioxanthen-9-one hydrochloride | thioxanthen-9-one with $CH_2-O-(CH_2)_3-\overset{+}{N}(CH_2CH_3)_2H \quad Cl^-$ |
| CCcompound 13 | 2-Hydroxy-N,N-dimethyl-N-[(9-oxo-9H-thioxanthen-2-yl)methyl]-ethanaminium bromide | thioxanthen-9-one with $CH_2-\overset{+}{N}(CH_3)_2-CH_2-CH_2-OH \quad Br^-$ |
| CCcompound 14 | 2-Hydroxy-N,N-Diethyl-N-[(9-oxo-9H-thioxanthen-2-yl)methyl]-ethanaminium bromide | thioxanthen-9-one with $CH_2-O-\overset{+}{N}(CH_2CH_3)_2-CH_2-CH_2-OH \quad Br^-$ |
| CCcompound 15 | 3-Hydroxy-N,N-dimethyl-N-[(9-oxo-9H-thioxanthen-2-yl)methyl]propane-1-aminium bromide | thioxanthen-9-one with $CH_2-\overset{+}{N}(CH_3)_2-CH_2-CH_2-CH_2-OH \quad Br^-$ |
| CCcompound 16 | 3-Hydroxy-N,N-diethyl-N-[(9-oxo-9H-thioxanthen-2-yl)methyl]-propane-1-aminium bromide | thioxanthen-9-one with $CH_2-\overset{+}{N}(CH_2CH_3)_2-CH_2-CH_2-CH_2-OH \quad Br^-$ |

TABLE 1-continued

A Representative List of CCcompounds Used in Embodiments of the Invention.

| Trivial name | Chemical name | Structure |
| --- | --- | --- |
| CCcompound 17 | 3-(9-hydroxy-9H-thioxanthen-9-yl)-N,N,N-trimethyl-propane-1-aminium iodide | 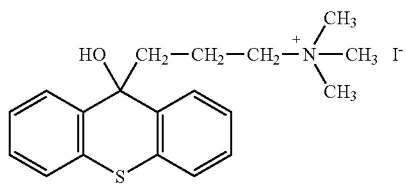 |
| CCcompound 18 | 3-(9-hydroxy-9H-selenoxanthen-9-yl)-N,N,N-trimethyl-propane-1-aminium iodide | 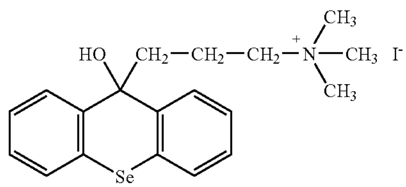 |
| CCcompound 19 | N,N,N-trimethyl-3-(9H-thioxanthen-9-ylidene)-propane-1-aminium iodide | 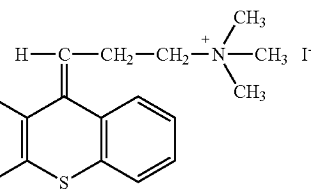 |
| CCcompound 20 | N,N,N-trimethyl-3-(9H-selenoxanthen-9-ylidene)-propane-1-aminium iodide | 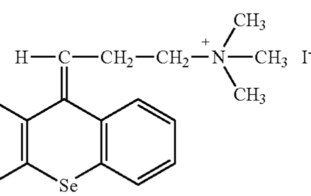 |
| CCcompound 21 | N,N,N-trimethyl-3-(2-methyl-9H-thioxanthen-9-ylidene)-propane-1-aminium iodide | 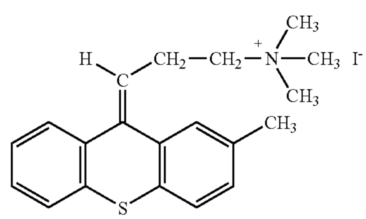 |
| CCcompound 22 | N,N-Dimethyl-N-ethyl-3-(2-methyl-9H-thioxanthen-9-ylidene)-propane-1-aminium iodide | 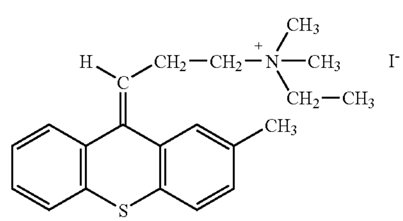 |
| CCcompound 23 | N,N-Diethyl-N-methyl-3-(2-methyl-9H-thioxanthen-9-ylidene)-propane-1-aminium iodide | 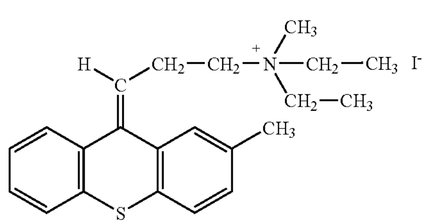 |

TABLE 1-continued

A Representative List of CCcompounds Used in Embodiments of the Invention.

| Trivial name | Chemical name | Structure |
| --- | --- | --- |
| CCcompound 24 | N,N-Dimethyl-N-allyl-3-(2-methyl-9H-thioxanthen-9-ylidene)-propane-1-aminium bromide | (structure) |
| CCcompound 25 | N,N,N-Triethyl-3-(2-methyl-9H-thioxanthen-9-ylidene)-propane-1-aminium iodidez | (structure) |
| CCcompound 26 | N,N-Diethyl-N-allyl-3-(2-methyl-9H-thioxanthen-9-ylidene)-propane-1-aminium bromide | (structure) |

II. Methods of Treatment.

Use of CC Compounds to Enhance Hematopoiesis from Endogenous Stem/Progenitor Cells in Patients Treated with Radiation Therapy or Myeloablative Chemotherapy.

Radiation treatment has long been known to negatively affect hematopoiesis. A large number of non-cell, cycle-dependent, anticancer drugs (for example, cyclophosphamide, chlorambucil, melphalan, busulfan, nitrosureas, thiotepa, nitrogen mustards) and anti-HIV protease inhibitors cause progressive depletion of hematopoietic stem cells resulting in late but long-lasting cytopenias. Many other drugs (for example, methotrexate, anthracyclines, etoposide, hydroxyurea, cytarabine) that are more effective against actively proliferating progenitors usually cause earlier and shorter-lasting cytopenias. When radiation or any cytopenia-causing drug is used for the treatment of cancer, AIDS or any other disease, a thioxanthone or thioxanthene CC compound listed in Table 1, such as for example CCompound1, CCompound3, or CCompound26, may be used to reduce or prevent cytopenias.

In one embodiment, oral application is one route to deliver a CC compound. CCompound1, CCompound3, CCompound26 and most of the other CC compounds listed in Table 1 are water-soluble. In one embodiment of the invention, the CC compound is in the form of a tablet, gel capsule, a liquid, or the like. In each case, the CC compound is mixed with one or more carriers selected to best suit the goal of treatment. In addition to the active compounds, the tablet or gel capsule may contain any component that is presently used in the pharmaceutical field to ensure firmness, stability, solubility and appropriate taste. Any additional component of the tablet or gel will be chemically inert; i.e., it will not participate in a chemical reaction with the CC compound or the other additives.

CC compounds may also be applied via intravenous, intraarterial, intraportal, intradermal, intraperitoneal, subcutaneous, intra-tissue or intramuscular delivery routes. In some embodiments, the CC compound may be delivered via infusion over a period of time or by using a minipump inserted under the skin. The injectable solution may be prepared by dissolving or dispersing a suitable preparation of the CC compound in a physiologically compatible carrier using conventional methods. For example, 0.9% sodium chloride (physiological saline) or phosphate buffered saline is appropriate to prepare the CC compound for injection. As an example only, a suitable composition for the practice in the method comprises a CC compound in a 0.9% physiological saline solution to yield a total CC compound concentrations of 1-g/ml or 2.5-g/ml.

A suitable dosage for oral or injection administration may be calculated in milligrams or grams of the active agent(s) per square meter of body surface area for the subject. In one embodiment, the therapeutically effective amount of CC compound is administered orally at a dose between 100-mg to 2,000-mg per $m^2$ body surface of the subject. In another embodiment, the CCompound is administered by an injection method at a dose of 50-mg to 1,000-mg per $m^2$ body surface of the subject.

The amount of the CC compound may vary depending on the method of application. For example, in case of intravenous application the required amount may approach the lower limit, while in case of subcutaneous application the required amount may be closer to the upper limit. In the case of oral application, more CC compound needs to be administered than in the case of injection methods.

Application of the CC compound orally or by one of the above injection application methods may be repeated as many times as needed to achieve a satisfactory level of re-population of the bone marrow as manifested in the normalization of blood cell and platelet counts in the peripheral blood.

In one embodiment, the therapeutically effective amount of CC compound may be administered once daily. In another embodiment, the dose is administered twice or three times daily. In still another embodiment, administration of the CC compound is performed three-times a week.

The half-life time of compounds that are structurally similar to CC compounds in the circulation is few minutes. Chen, C.-L., Malaviya, R., Navara, C., Chen, H., Bechard, B., Mitcheltree, G., Liu, X.-P. and Uckun, F. M., "Pharmacokinetics and biologic activity of the novel mast cell inhibitor, 4-(3'-hydroxyphenyl)-amino-6,7-dimethylquinazoline in mice," *Pharmaceutical Res.*, 15, 117-122 (1999). Since the half-life time of the CC compounds may also be minutes rather than hours, one suitable application is once or twice a day.

An important decision that the health care provider needs to make concerns the start and the length of treatment with the CC compound in relation to protecting bone marrow stem/progenitor cells. Since CC compound protects the bone marrow stem/progenitor cells against radiation- and chemotherapy-induced damage, it is recommended that its administration starts prior to the start of radiation or chemotherapy and continues during and after finishing a single therapy or the therapy cycle. Resting periods of various lengths, depending on the intensity and frequency of radiation or drug treatment, may be applied between cycles of CC compound administration.

The CC compound is used together with one or more treatments in embodiments of the invention. However, in addition to the radiation therapy or drug used to treat the primary disease, the CC compound may also be used together with other agents or enhancers that positively influence(s) the proliferation and/or survival of bone marrow stem/progenitor cells as well as survival of differentiated cells. Examples for such agents or enhancers include cytokines and growth factors such as G-CSF, GM-CSF, erythropoietin, interleukin-3, interleukin-11, insulin-like growth factor-1, insulin, growth hormone, platelet-derived growth factor, fibroblasts growth factor, placental growth factor, epidermal growth factor, vascular endothelial growth factor, transforming growth factors as well as testosterone and amino acids such as leucine. In addition, a CC compound may also be administered together with nutraceuticals, such as freeze-dried blueberry extract, green tea extract, carnosine, catechin and the activated form of vitamin $D_3$. These nutraceuticals were shown to enhance proliferation of human bone marrow-derived hematopoietic stem cells. Biskford, P. C., Tan, J., Shytle, R. D., Sanberg, C. D., El-Badri, N. and Sanberg, P. R., "Nutraceuticals synergistically promote proliferation of human stem cells," *Stem Cells and Development*, 15, 118-123 (2006).

In the case of oral administration of the CC compound, enhancers may be applied separately from the CC compound. In the case of injection application, the enhancers and the CC compound may be dissolved or suspended in the same physiologically compatible carrier, or they may be applied separately.

Use of CC Compounds to Enhance Hematopoiesis from Exogenous Stem/Progenitor Cells After Bone Marrow Transplantation.

For the present application, first bone marrow is completely destroyed by total body irradiation or a combination of high dose chemotherapy and total body irradiation. The purpose of such extreme treatments is to eliminate all cancerous cells that may reside in the bone marrow (leukemia cells or metastasized tumor cells derived from solid tumors). This procedure is followed within a short time period by transplantation of bone marrow stem/progenitor cells. It is important that a CC compound is not applied during the preparatory irradiation/chemotherapy treatment because it may interfere with the process of eliminating stem cell precursors of cancer cells.

Adult stem/progenitor cells used for re-populating the empty bone cavity may be obtained directly from the bone marrow (for example, from posterior iliac crests), or from peripheral blood. In the latter case, the donor (the patient himself/herself or a close relative) may be pretreated with G-CSF and/or GM-CSF to mobilize bone marrow cells and enhance the yield of peripheral blood progenitor cells. The stem/progenitor cell population may be enriched by various methods, for example by using magnetic-activated cell sorting to remove monocytes or T-lymphocytes or Ficoll-Hypaque density gradient centrifugation. Prior to transplantation, the stem/progenitor cells are usually stored in a 5-20% dimethylsulfoxide-containing medium such as Iscove's modified Dulbecco's medium in the vapor phase of liquid nitrogen. Any standardized procedures for the isolation, enrichment and storage of stem/progenitor cells that are well known in the art may be used.

A CC compound used in conjunction with bone marrow transplantation may be used to decrease the time interval needed for the recipient to reach appropriate levels of white blood cells and platelets to fight infection and control bleeding. In human cancer patients, administration of G-CSF following stem cell transplantation helps to recover the white blood cell count to 2,500 per 1 µl ($mm^3$) after about 10 days and the platelet count to about 100,000 per 1 µl after about 14 days. Ballestrero, A., Ferrando, F., Garuti, A., Basta, P., Gonella, R., Stura, P., Mela, G. S., Sessarego, M, Gobbi, M. and Patrone, F., "Comparative effects of three cytokine regimens after high-dose cyclophosphamide: Granulocyte colony-stimulating factor, granulocyte-macrophage colony-stimulating factor (GM-CSF), and sequential interleukin-3 and GM-CSF," *J. Clin. Oncol.*, 17, 1296-1303 (1999). Administration of CCompound1 helped to recover similar counts of white blood cells and platelets from transplanted bone marrow stem cells after about 9-11 days and less than 6 days, respectively.

In some embodiments, the CC compound is included in a stem cell-containing infused solution. The CC compound is dissolved in the same solution that is used for the infusion. For example, either Iscove's modified Dulbecco's medium or 0.9% sodium chloride (physiological saline) is an appropriate solute for infusion. The amount of the CC compound administered may vary between 50-1,000-mg per $m^2$ of body surface. In some other embodiments, the CC compound is delivered intravenously, intraperitoneally, subcutaneously, intraarterially, intraportally, intradermally or using a minipump independent of the injected bone marrow stem cells shortly before or after the transplantation procedure.

The CC compound may also be administered orally at a dose between 100-mg to 2,000-mg per $m^2$ of body surface shortly (several hours) before or soon after stem cell transplantation.

In most cases, transplantation of the stem/progenitor cells will likely to be a single event due to the limited supply of cells and safety reasons. However, application of the same or less amounts of the CC compound by one of the above application methods may be repeated as many times as needed to ensure the survival and in vivo propagation of the transplanted cells. For example, in case of subjects receiving bone marrow-derived stem/progenitor cell transplantation, a CC compound may be administered for up to about 40 days on a regular basis (once or twice daily with some resting periods included as required) for promoting regeneration of bone marrow.

With respect to the addition of enhancers together with the CC compound after stem/progenitor stem cell transplantation the same applies that is described earlier. For example, the most important enhancers that may be used together with a CC compound are G-CSF, GM-CSF, erythropoietin, interleukin-3, and interleukin-13.

EXAMPLES

Example 1

Effects of CCompound1, CCompound3 and CCompound26 on Blood Profile in Cyclophosphamide-Treated Mice Twelve week old female C57B1 mice were used for the experiments. Each drug was administered intraperitoneally once a day for 5 consecutive days. In the second, third, fourth and fifth groups, mice were administered 120 mg/kg of cyclophosphamide (CP). In a third group, mice were also administered 4.5 mg/kg of CCompound1. In a fourth group, mice were also administered 4.5 mg/kg of CCompound3. In a fifth group, mice were also administered 2.0 mg/kg of CCompound26. In the first group, mice received no treatment. Each group included 5 animals. After 3 hours of the last treatments (on day 5), blood samples were collected from the ocular venous plexus of ether-anesthetized mice by retro-orbital venipuncture in heparanized tubes. Complete cell counts (RBC, red blood cell; WBC, white blood cell; PTL, platelet) were determined with a Sysmex F-800 hematology analyzer (To a Medical Electronics Co. LTD, Kobe, Japan). All data shown in Table 2 are the average of 5 independent determinations.

The data indicate that CP decreases both WBC and PTL numbers. Each CC compound improved the blood profile with CCompound26 being the least effective. However, it should be noted that CCompound26 was used at a smaller dose than the two other CC compounds.

TABLE 2

CC compounds improve the blood profile in cyclophosphamide-treated mice.

| Treatment | RBC; ×10$^6$/μl | WBC; ×10$^6$/μl | PTL; ×10$^3$/μl |
|---|---|---|---|
| None | 9.7 ± 0.6 | 6.8 ± 1.2 | 967 ± 73 |
| CP | 8.1 ± 0.9 | 3.2 ± 0.7 | 404 ± 55 |
| CP + CCcompound1 | 9.5 ± 0.7 | 5.8 ± 1.3 | 803 ± 81 |
| CP + CCcompound3 | 9.3 ± 1.1 | 6.2 ± 0.8 | 846 ± 92 |
| CP + CCcompound26 | 8.9 ± 0.5 | 5.1 ± 0.6 | 687 ± 62 |

Example 2

This experiment was designed to determine whether in a tumor model CC compounds could prevent cyclophosphamide-induced loss of body weight resulting from the depression of blood marrow function. Specified pathogen free (SPF) hygienic category colonies of first generation hybrid BDF1 (C57B1 female×DBA/2 male) adult female mice, weighing 23-24 g, were used. The animals were kept in macrolon cages at 22-24° C. (45-55% humidity), with a lighting regimen of 12/12 h light/dark. The animals had free access to tap water and were fed with a sterilized standard diet (Charles River VRF1, autoclavable, Germany) ad libitum. The animals used in these studies were cared for according to the "Guiding Principles for the Care and Use of Animals" based upon the Helsinki declaration.

MXT mammary tumor pieces (containing about $10^6$ tumor cells) were implanted subcutaneously to develop the tumors. After six days when the tumor-bearing mice were first treated, the sizes of the tumors were in the 0.26-0.30 cm$^3$ range. All compounds used were dissolved in 0.9% sodium chloride and applied subcutaneously (CC compounds) or intraperitoneally (CP) in 50 μl volume. Tumor volume was determined by using calipers in three dimensions; this technique is well known to one having ordinary skill in the art. Tumor volume was calculated according to the generally accepted formula: $V=a^2 \times b \times \pi/6$, where "a" and "b" mean the shortest and longest diameter, respectively, of the measured tumor.

In the first group, animals received no treatment. In the second group, mice were administered 120-mg/kg of CP on day 6 followed by seven consecutive daily treatments with the same dose. In the third group, each treatment with CP was associated with administration of 4.5-mg/kg of CCompound1. In the fourth group, each treatment with CP was associated with administration of 4.5-mg/kg of CCompound3. In the fifth group, each treatment with CP was associated with administration of 2.0-mg/kg of CCompound26. Each group included 7 mice. All data represent the average of 7 determinations (one determination with each mouse in the group).

Data in Table 3 show that treatments with CP effectively decreased tumor weight and that none of the CC compounds interfered with the tumor-reducing action of CP. Both untreated and particularly CP-treated mice lost significant amounts of weight by day 22 (Table 3). In contrast, administration of CCompound26 to CP-treated mice prevented body weight loss, while administration of both CCompound1 and particularly CCompound3 resulted in body weight gain (Table 3). Thus, the positive effects of CC compounds on blood profile in CP-treated mice (Table 2) were associated with protection of body weight.

TABLE 3

CC compounds prevent tumor- and cyclophosphamide-induced body weight loss in the MXT tumor model.

| Treatment | Weight (in grams) | Days after tumor transplantation | | | | | |
|---|---|---|---|---|---|---|---|
| | | 6 | 8 | 11 | 15 | 18 | 22 |
| None | Total weight | 22.3 | 22.8 | 22.9 | 25.3 | 26.0 | 26.2 |
| | Tumor weight | 0.2 | 0.4 | 1.3 | 2.2 | 4.3 | 6.7 |
| | Body weight | 22.1 | 22.4 | 21.6 | 23.1 | 21.7 | 19.5 |
| CP | Total weight | 22.4 | 21.8 | 20.2 | 19.9 | 18.8 | 18.1 |
| | Tumor weight | 0.2 | 0.2 | 0.1 | 0.2 | 0.1 | 0.1 |
| | Body weight | 22.2 | 21.6 | 20.1 | 19.7 | 18.7 | 18.0 |
| CP + CCcompound1 | Total weight | 22.3 | 22.1 | 22.2 | 22.3 | 22.8 | 23.3 |
| | Tumor weight | 0.2 | 0.3 | 0.1 | 0.1 | 0.1 | 0.1 |
| | Body weight | 22.1 | 21.8 | 22.1 | 22.2 | 22.7 | 23.2 |
| CP + CCcompound3 | Total weight | 22.1 | 21.9 | 22.9 | 23.5 | 24.0 | 24.8 |
| | Tumor weight | 0.2 | 0.2 | 0.2 | 0.2 | 0.1 | 0.1 |
| | Body weight | 21.9 | 21.7 | 22.7 | 23.3 | 23.9 | 24.7 |
| CP + CCcompound26 | Total weight | 22.2 | 22.0 | 22.1 | 21.8 | 22.1 | 22.2 |
| | Tumor weight | 0.2 | 0.3 | 0.2 | 0.1 | 0.1 | 0.1 |
| | Body weight | 22.0 | 21.7 | 21.9 | 21.7 | 22.0 | 22.1 |

Example 3

CCompound1 Promotes Recovery of Bone Marrow Function After Sublethal Whole Body Irradiation This experiment served to determine if CCompound1 was able to promote regeneration of partially ablated bone marrow from endogenous stem cells i.e. promote restoration of the capacity of bone marrow to produce blood cells. The CFU-GM assay was performed because the number of CFU-GM per femur is a good indicator of bone marrow regeneration. Ballestrero, A., Ferrando, F., Garuti, A., Basta, P., Gonella, R., Stura, P., Mela, G. S., Sessarego, M, Gobbi, M. and Patrone, F., "Comparative effects of three cytokine regimens after high-dose cyclophosphamide: Granulocyte colony-stimulating factor, granulocyte-macrophage colony-stimulating factor (GM-CSF), and sequential interleukin-3 and GM-CSF," *J. Clin. Oncol.*, 17, 1296-1303 (1999).

C57B1 female (10-14 weeks old) mice received sublethal (250 cGy) whole body irradiation from a $^{137}$Cesium source (day 0). Starting three days before irradiation, animals received daily 4.5 mg per kg of CCompound1 via intraperitoneal injection; this treatment also was provided on day 0 and once daily for three days subsequent to irradiation. In another group, mice were injected only with physiological saline. The subsequent procedure has been reported in Vas, V., Fajka-Boja, R., Ion, G. A., Dudics, V., Monostori, E. and Uher, F., "Biphasic effect of recombinant Galectin-1 on the growth and death of early hematopoietic cells," *Stem Cells*, 23, 279-287 (2005). Briefly, bone marrow was flushed from the femurs with Iscove's modified Dulbecco's medium (Gibco BRL, Gaithersburg, Md., USA), and after standard erythrocyte lysis, nucleated cells were counted using a hemocytometer. Samples were taken on days 0, 1, 3, and 10. To measure the formation of the granulocyte-macrophage colony-forming units (CFU-GM), a semisolid colony-forming cell assay was used. Nucleated bone marrow cells (isolated on the days as indicated above) were plated in 35-mm Petri dishes (Costar, Cambridge, Mass., USA) in Iscove's modified Dulbecco's medium supplemented with 1% methylcellulose, 30% horse serum (Gibco), 10% WEHI-3B conditioned medium as a source of growth factors, 4 mM L-glutamine, 0.25 mM a-thioglycerol (Gibco), 1% deionized bovine serum albumine (Sigma), and antibiotics (Gibco). Cells were cultured at 37° C. in 5% $CO_2$/95% air atmosphere and colonies were counted on day 7 in the same dish. Colonies containing at least 50 cells were counted which is a generally accepted value in the literature. Each value represents the mean ±st. dev. of 9 samples (3 parallel dishes from each animal).

Data in Table 4 indicate that from the third day on, injected CCompound1 enhanced the number of nucleated bone marrow cells and CFU-GM. This is an indication that CCompound1 proportionally increased the number of CFU-GM per femur. Overall, the experiment indicated that CCompound1 enhanced regeneration of bone marrow from endogenous stem/progenitor cells after a sublethal reduction in the number of bone marrow cells. Considering these data and data in Table 2 showing that CCompound3 and CCompound26 along with CCompound1 improved blood cell recovery in cyclophosphamide-treated animals, CCompound3 and CCompound26 are also capable of promoting bone marrow recovery in mammals subjected to sublethal irradiation.

TABLE 4

CCcompound1 promotes recovery of bone marrow function after sublethal irradiation.

| Time* (days) | CCcompound1 treatment | Nucleated BM* cells per femur ($\times 10^{-6}$) | CFU-GM/$10^5$ nucleated BM cells | CFU-GM per femur |
|---|---|---|---|---|
| 0 | No | 13.97 ± 0.71 | 67.3 ± 4.4 | 940 |
| 1 | No | 3.63 ± 0.64 | 46.1 ± 4.3 | 167 |
| 3 | No | 2.42 ± 0.33 | 60.7 ± 8.7 | 147 |
| 3 | Yes | 5.79 ± 0.22 | 87.8 ± 9.0 | 508 |
| 6 | No | 3.86 ± 0.39 | 80.8 ± 7.9 | 312 |
| 6 | Yes | 7.73 ± 0.25 | 92.3 ± 7.2 | 713 |
| 10 | No | 7.64 ± 0.69 | 76.5 ± 5.0 | 584 |
| 10 | Yes | 11.45 ± 0.81 | 94.4 ± 8.1 | 1,081 |

*Days after irradiation when bone marrow was harvested;
**BM is bone marrow.

Example 4

CCompound1 Promotes Expansion of Transplanted Bone Marrow Cells and Restoration of Normal Blood Profile In this experiment the goal was to determine if CCompound1 can enhance expansion of transplanted bone marrow cells infused after applying a lethal dose of whole body irradiation (which reduces the number of bone marrow cells by more than 90%). C57B1 female mice (10-14 weeks old) were subjected to 900 cGy whole body irradiation from a $^{137}$Cesium source which was followed within 6 hours by infusion of one million donor nucleated bone marrow cells by tail vein injection. Starting 3 days before irradiation, animals received daily 4.5 mg per kg of CCompound1 via intraperitoneal injection; this treatment also was provided on day 0 and once daily for the subsequent 3 days after irradiation. In another group, mice were injected only with physiological saline.

Bone marrow cells were collected on day 0 from non-irradiated animals as well as on days 6, 14, 28 and 42 after irradiation and bone marrow transplantation. Nucleated bone marrow cells were quantified and CFU-GM assay was performed as described in Example 3 while blood profiling was performed as described in Example 1. For each group, on the indicated days bone marrow and blood samples were collected from 3 animals. Each value presented in Table 5 and Table 6 represents the mean ±st. dev. of 3 samples (derived from 3 animals).

The results show that by day 6 and 14 following transplantation, in the CCompound1-treated animals the level of bone marrow re-population in the femur was about 5.3-fold and 2.9-fold greater, respectively, than in the untreated animals (Table 5). This was accompanied by significantly greater level of recovery of white blood cell and platelet counts in the peripheral blood of the CCompound1-treated animals (Table 6). It is important to note here that the speed by which bone marrow regains its function is important because the faster the bone marrow regeneration is the less likely that infection will lead to complications often resulting in death. In CCompound1-treated animals about 50% recovery of white blood cells took about 14 days. The same level of recovery in untreated animals is likely to take about 22 days based on the kinetics of white blood cell counts (Table 6). Similarly, the rapid rise in platelet counts in CCompound1-treated animals suggests that if bone marrow transplantation is accompanied by treatment with a CC compound, the transplant recipient may not require platelet transfusion to achieve a necessary level of platelet count to avoid potential complications resulting from internal bleeding.

Another important finding was that the effects of CCompound1 lasted for a remarkably long time period. Even though the last treatment was on day 3 after transplantation, CCompound1 still clearly had significant effects on day 14 both on CFU-GM and the white blood cell and platelet counts. It is reasonable to expect that longer treatment with CCompound1 or another CC compound could result in an even more rapid and more extensive recovery of normal blood profile between days 6 and 28.

TABLE 5

CCcompound1 enhances bone marrow regeneration from transplanted bone marrow cells after lethal irradiation.

| Time* (days) | Treatment | BM** cells per femur ($\times 10^{-6}$) | CFU-GM/$10^5$ nucleated BM cells | CFU-GM per femur |
|---|---|---|---|---|
| 0  | None        | 14.70 ± 1.33 | 72.5 ± 4.7  | 1065.8 |
| 6  | None        | 0.87 ± 0.22  | 29.3 ± 5.4  | 25.5   |
| 6  | CCcompound1 | 3.01 ± 0.49  | 44.8 ± 5.1  | 134.9  |
| 14 | None        | 3.52 ± 1.03  | 62.8 ± 6.1  | 221.1  |
| 14 | CCcompound1 | 8.01 ± 1.55  | 81.2 ± 5.3  | 650.4  |
| 28 | None        | 8.45 ± 1.20  | 119.5 ± 7.9 | 1,009.8 |
| 28 | CCcompound1 | 10.25 ± 1.74 | 125.5 ± 9.1 | 1,286.4 |
| 42 | None        | 13.90 ± 0.84 | 69.2 ± 5.4  | 961.9  |
| 42 | CCcompound1 | 13.88 ± 1.57 | 71.5 ± 5.3  | 992.4  |

TABLE 6

CCcompound1 promotes restoration of normal blood profile after bone marrow transplantation following lethal irradiation.

| Time (days) | Treatment | RBC ($\times 10^6/mm^3$) | WBC ($\times 10^3/mm^3$) | Platelets ($\times 10^3/mm^3$) |
|---|---|---|---|---|
| 0  | None        | 9.1 ± 0.7  | 6.8 ± 0.3 | 923 ± 110 |
| 6  | None        | 3.1 ± 1.1  | 0.2 ± 0.1 | 103 ± 20  |
| 6  | CCcompound1 | 4.8 ± 1.2  | 1.6 ± 0.3 | 243 ± 19  |
| 14 | None        | 8.2 ± 1.2  | 0.9 ± 0.2 | 239 ± 27  |
| 14 | CCcompound1 | 9.1 ± 1.1  | 3.3 ± 0.4 | 438 ± 112 |
| 28 | None        | 10.2 ± 0.8 | 4.3 ± 0.7 | 761 ± 119 |
| 28 | CCcompound1 | 10.9 ± 1.3 | 5.2 ± 0.8 | 716 ± 138 |
| 42 | None        | 9.5 ± 0.5  | 7.3 ± 0.5 | 794 ± 147 |
| 42 | CCcompound1 | 11.0 ± 0.7 | 6.6 ± 0.4 | 776 ± 112 |

Example 5

Effects of CCompound1 on the Survival and Proliferation of Human Bone Marrow-Derived Mesenchymal Stem Cells in the Absence of Serum These experiments were designed to test the possibility that CCompound1 directly promotes survival and/or proliferation of stem cells in the absence or presence of 2% serum, respectively.

Bone marrow aspirates were taken from normal adult donors after an informed consent was signed. Bone marrow mesenchymal stem cells were prepared by a widely used technique as described earlier by others. Pittenger, M. F., Mackay, A. M., Beck, S. C., Jaiswal, R. K., Douglas, R., Mosca, J. D., Moorman, M. A., Simonetti, D. W., Craig, S, and Marshak, D. R., "Multilineage potential of adult human mesenchymal stem cells," Science, 284, 143-147 (1999). Briefly, nucleated cells were isolated with a pre-prepared commercial density gradient (Lymphoprep, Nycomed, Pharma, Oslo, Norway) and resuspended in Dulbecco's modified Eagle's medium (DMEM)(GIBCO, Grand Island, N.Y.) supplemented with 10% fetal calf serum (FCS), 50 U/ml of penicillin, and 50 µg/ml of streptomycin (GIBCO). All nucleated cells were plated in 25-cm$^2$ flasks (BD Falcon, Bedford, Mass.) at 37° C. in humidified atmosphere containing 5% $CO_2$. After 24 hours, nonadherent cells were removed and cryopreserved in liquid nitrogen until use. The remaining adherent cells were thoroughly washed with Hanks balanced salt solution (HBSS)(GIBCO). Fresh complete culture medium was added and replaced every 3 or 4 days (twice a week). When cells grew to about 80% confluence, they were suspended and harvested by incubating with a ready-made solution containing 0.25% trypsin and 1 mM EDTA (Sigma-Aldrich, St. Louis, Mo.) for 5 minutes at 37° C.; this cell suspension is designated as passage 1. These cells were further expanded with 1:3-1:5 splitting in 175-cm$^2$ flasks (BD Falcon). In the studies reported in this invention, mesenchymal stem cells were used between passages 3-8.

The total numbers of nucleated and viable cells were determined with a hemocytometer, using Turck's solution and trypan blue stain, respectively. The morphology of mesenchymal stem cells was examined every week under an inverted microscope (Olympos CK2, Tokyo, Japan) to verify that cells retained their structural characteristics.

In the experiments reported in Table 7 and Table 8, human bone marrow-derived mesenchymal stem cells were split at 1:3 and then incubated for 24 hours in 10% fetal calf serum-containing medium to about 30-35% confluence. Then the medium was replaced with fresh serum-free medium (Table 7) or with a medium containing 2% serum (Table 8). After about 2 hours, the cells remained either untreated or were treated with 10 µM or 50 µM concentrations of CCompound1. Then the incubations were continued for up to 6 days followed by the determination of viable cell number. The data are expressed as mean values ±std. dev. of 3 determinations.

The results in Table 7 show while 10 µM CCompound1 had the tendency to slightly enhance cell numbers, the effects did not reach statistical significance. At 50 µM concentration CCompound1 clearly had no effect. The results presented in Table 8 also indicate that CCompound1 has no direct stimulatory effect on the proliferation of stem cells. Overall, these experiments indicated that CCompound1 is unlikely to directly affect survival or proliferation of hematopoietic stem/progenitor cells that could explain its effects in vivo on CFU-GM and peripheral blood profile. Hence one has to assume that CCompound1 acts on bone marrow regeneration via one or more indirect mechanism(s) such as, for example, stimulation of growth factor expression.

TABLE 7

CCcompound1 does not significantly promote survival of mesenchymal stem cells in the absence of serum.

| Incubation | Cell number per culture ($\times 10^{-3}$); 0% serum | | |
|---|---|---|---|
| time (day) | None | CCcompound1, 10 µM | CCcompound1, 50 µM |
| 0 | 20        | 20        | 20        |
| 2 | 4.2 ± 1.6 | 6.9 ± 2.2 | 4.8 ± 1.9 |
| 4 | 4.7 ± 2.0 | 5.1 ± 2.4 | 4.0 ± 1.3 |
| 6 | 5.1 ± 2.3 | 6.2 ± 1.4 | 5.4 ± 1.7 |

TABLE 8

CCcompound1 does not significantly promote proliferation of mesenchymal stem cells in the presence of 2% serum.

| Incubation time (day) | Cell number per culture (×10⁻³); 2% serum | | |
|---|---|---|---|
| | None | CCcompound1, 10 μM | CCcompound1, 50 μM |
| 0 | 20 | 20 | 20 |
| 2 | 4.8 ± 2.2 | 5.9 ± 1.6 | 5.4 ± 1.4 |
| 4 | 7.3 ± 1.8 | 8.2 ± 3.3 | 6.2 ± 2.1 |
| 6 | 13.8 ± 3.2 | 15.4 ± 3.1 | 12.0 ± 4.4 |

Example 6

Effects of CCompound1 on the Viability of Other Cell Lines

These experiments were designed to determine if CCompound1 promotes the survival and/or proliferation of the following types of normal and cancer cells.

The NIH 3T3 (normal) mouse fibroblast, A431 human epidermoid adenocarcinoma, and MCF-7 human breast cancer cells were cultured in DMEM medium containing 10% FBS. The MEL-28 human melanoma cells were cultured in MEM medium containing 10% FBS. The HT-29 human colon adenocarcinoma cells were cultured in McCoy's 5a medium containing 10% FBS. The A549 human lung carcinoma cells were maintained in Ham's F12K medium containing 10% FBS. T47D cells were cultured in 12-well plates in RPMI 1640 medium supplemented with 0.2 IU bovine insulin and 10% FBS. CaOV-3 human ovarian cancer cells were cultured in DMEM containing 10% FBS. ZR-75-1 human estrogen receptor-positive breast cancer cells were maintained in RPMI 1640 medium supplemented with 10% FBS. HTB-157 human fetal fibroblasts, MEL-24 human malignant melanoma cells, Hep G2 human hepatoblastoma cells, and CaCO-2 human colon adenocarcinoma cells were maintained in Eagles's MEM containing 10% FBS. MB-231 human estrogen receptor-negative breast cancer cells were maintained in Leibovitz's L-15 medium supplemented with 10% FBS.

In the actual experiments, cells were seeded into 96-well plates and cultivated up to either ~70-90% confluency (survival experiments) or 20-25% confluency (proliferation experiments). Then the medium was changed for serum-free medium (survival experiment) or 2% serum-containing medium (proliferation experiment). The incubation continued for 72 hours followed by the MTT assay to determine cell viability. This colorimetric assay is based on the ability of living cells, but not dead cells, to reduce 3-(4,5-dimethyl thiazol-2-yl)-2,5-diphenyltetrazolium bromide. Carmichael, J, De Graff, W. G., Gazdar, A. F., Minna, J. D. and Mitchell, J. B., "Evaluation of tetrazolium-based semiautomated colorimetric assay: Assessment of chemosensitivity testing," Cancer Res., 47, 936-942 (1987).

Neither the lower nor the higher concentration of CCompound1 enhanced the survival or proliferation of either cell types listed above. At the higher (50 μM) concentration, CCompound1 decreased the viability of CaOV-3, Hep G2, ZR-75-1, and MEL-28 cells by about 20-40%. Overall, these series of experiments indicate that in vitro CCompound1 has no direct positive effects on the survival and proliferation of normal and cancer cells. Therefore, these experiments indicate that in vivo CCompound1 may promote restoration of bone marrow function by an indirect, presently unknown, mechanism(s).

What is claimed is:

1. A method of regenerating bone marrow comprising: administering a composition to a subject comprising a heterocyclic compound, thereby normalizing blood cell and platelet counts, wherein the compound is represented by the formula:

[chemical structure of thioxanthene-type compound with substituents $R_1$–$R_{10}$, V, Y, and counterion $Z^-$]

wherein R1 and R3-8 are independently hydrogen, C1-C26 straight, branched or cyclic alkanes or alkenes, aromatic hydrocarbons, alcohols, ethers, aldehydes, ketones, carboxylic acids, amines, amides, nitriles or five- and/or six-membered heterocyclic moieties;
wherein R9 and R10 considered together are =O or =CH—L—N⁺(R11, R12, R13) or wherein R9 and R10 considered independently are —OH or —L—N⁺(R11, R12, R13);
wherein R2 is represented by the formula: —X or —X'—L—N⁺(R11, R12, R13)Z—;
wherein V is —S—, —Se—, —C—, —O— or —N;
wherein Y is —S—, —Se—, —C—, —O— or —N;
wherein —L—N⁺(R11, R12, R13) is linked to V;
wherein X is CH3;
wherein —X' is —CH2—, —OCH2—, —CH2O—, —SCH2— or —CH2S—;
wherein L is a C1-C4 straight alkane, alkene, thiol, ether, or amine;
wherein R11, R12 and R13 are independently C1-C4 straight alkanes, alkenes, thiols, amines, ethers or alcohols; and
wherein Z is Cl—, Br— or I—.

2. The method of claim 1 wherein R11, R12, and R13 are independently methyl, ethyl, propyl, allyl, ether, sulfhydryl, amino, or hydroxyl groups.

3. The method of claim 1 wherein the compound is a thioxanthone.

4. The method of claim 3 wherein R9 and R10 considered together are =O and R2 is —X—L—N⁺(R11, R12, R13)Z—.

5. The method of claim 3 wherein the compound is [3-(3,4-dimethyl-9-oxo-9H-thioxanthen-2-yloxy)-2-hydroxypropyl]trimethylammonium chloride.

6. The method of claim 3 wherein the compound is N,N,-diethyl-N-methyl-2-[9-oxo-9H-thioxanthen-2-yl)methoxy]ethanaminium iodide.

7. The method of claim 1 wherein the compound is a thioxanthene.

8. The method of claim 7 wherein R2 is O or X and R9 and R10 considered together are =CH—L—N⁺(R11, R12, R13); L is —(CH2)2— or —(CH2)3—; and R1 and R3-8 are hydrogen.

9. The method of claim 7 wherein the compound is N,N-Diethyl-N-allyl-3-(2-methyl-9H-thioxanthen-9-ylidene)-propane-1-aminium bromide.

10. The method of claim 1 wherein the heterocyclic compound is administered orally in the form of a tablet, gel capsule, or liquid.

11. The method of claim 10 wherein the heterocyclic compound is administered orally at a dose between 100-mg to 2,000-mg per $m^2$ body surface of a subject.

12. The method of claim 10 wherein the heterocyclic compound is administered once or twice daily.

13. The method of claim 1, wherein the heterocyclic compound is injected via intravenous, intraarterial, intraperitoneal, subcutaneous, intramuscular, or intradermal routes.

14. The method of claim 13, wherein the heterocyclic compound is administered by infusion or an implanted minipump in a controlled fashion.

15. The method of claim 13 wherein the heterocyclic compound is administered at a dose between 50-mg to 1,000-mg per $m^2$ body surface of the subject.

16. The method of claim 1 wherein the heterocyclic compound is administered together, simultaneously or sequentially, with one or more promoters of bone marrow regeneration.

17. The method of claim 16 wherein the promoters of bone marrow regeneration are granulocyte-macrophage colony-stimulating factor, granulocyte colony-stimulating factor, interleukin-3, interleukin-11, erythropoietin, or thrombopoietin.

18. The method of claim 1 wherein the bone marrow is regenerated from endogenous or exogenous hematopoietic stem/progenitor cells and the heterocyclic compound normalizes blood cell and platelet counts.

19. The method of claim 1 wherein the heterocyclic moiety compound is administered to a subject requiring improved bone marrow function and increased hematopoiesis.

20. The method of claim 19 wherein the subject receives no additional therapy or receives chemotherapy or radiation therapy before, during or after administration of the heterocyclic moiety.

* * * * *

UNITED STATES PATENT AND TRADEMARK OFFICE
CERTIFICATE OF CORRECTION

| | | |
|---|---|---|
| PATENT NO. | : 7,423,029 B1 | |
| APPLICATION NO. | : 11/690260 | |
| DATED | : September 9, 2008 | |
| INVENTOR(S) | : Zoltan Kiss | |

It is certified that error appears in the above-identified patent and that said Letters Patent is hereby corrected as shown below:

Column 22
Line 44, delete the phrase "wherein Z is" and replace it with -- wherein Z- is --

Column 24
Line 11, delete the word "moiety"

Signed and Sealed this

Twenty-fifth Day of November, 2008

JON W. DUDAS
*Director of the United States Patent and Trademark Office*